United States Patent
Schedler et al.

(10) Patent No.: US 11,944,845 B2
(45) Date of Patent: *Apr. 2, 2024

(54) ASYMMETRIC DUAL-MODE IONIZATION SYSTEMS AND METHODS

(71) Applicant: Varian Medical Systems Particle Therapy GmbH & Co. KG, Troisdorf (DE)

(72) Inventors: Manuel Schedler, Bonn (DE); Simon Busold, Cologne (DE); Birger Schumacher, Kurten (DE)

(73) Assignee: VARIAN MEDICAL SYSTEMS PARTICLE THERAPY GMBH & CO. KG, Troisdorf (DE)

(*) Notice: Subject to any disclaimer, the term of this patent is extended or adjusted under 35 U.S.C. 154(b) by 0 days.

This patent is subject to a terminal disclaimer.

(21) Appl. No.: 18/088,242

(22) Filed: Dec. 23, 2022

(65) Prior Publication Data

US 2023/0125731 A1 Apr. 27, 2023

Related U.S. Application Data

(63) Continuation of application No. 17/219,542, filed on Mar. 31, 2021, now Pat. No. 11,534,626.

(51) Int. Cl.
*A61N 5/10* (2006.01)

(52) U.S. Cl.
CPC .... *A61N 5/1048* (2013.01); *A61N 2005/1087* (2013.01)

(58) Field of Classification Search
CPC .......... A61N 5/1048; A61N 2005/1087; G01T 1/185; G01T 1/14; G01T 1/142; G01T 7/005; H01J 47/02
See application file for complete search history.

(56) References Cited

U.S. PATENT DOCUMENTS

| | | | |
|---|---|---|---|
| 3,008,051 A | 11/1961 | Pocock | |
| 5,693,947 A | 12/1997 | Morton | |
| 6,133,575 A | 10/2000 | Charpak et al. | |
| 9,408,286 B1 * | 8/2016 | Elizondo-Decanini | ...................... H05H 5/047 |
| 9,978,554 B1 * | 5/2018 | Koo | .......................... H01J 1/50 |
| 11,534,626 B2 * | 12/2022 | Schedler | ................. G01T 1/185 |

(Continued)

*Primary Examiner* — Marcus H Taningco
(74) *Attorney, Agent, or Firm* — Harness, Dickey & Pierce, P.L.C.

(57) ABSTRACT

An asymmetric dual-mode ionization chamber measurement system can include a first high-voltage plate, a second high-voltage plate and a readout plate. The first high-voltage plate can be disposed from the readout plate by a first active volume. The second high-voltage plate can be disposed from the readout plate by a second active volume. A high-voltage potential can be coupled to the first high-voltage plate during a first mode, and to the second high-voltage plate during a second mode. Ion pairs generated by a radiation stream passing through the first active volume during the first mode and the second active volume during the second mode can be measured at the readout plate to determine a radiation rate of the ionizing radiation. The asymmetric dual-mode ionization chamber measurement system can advantageously measure different radiation streams that have significantly different ranges of radiation rates flux.

21 Claims, 3 Drawing Sheets

(56) References Cited

U.S. PATENT DOCUMENTS

| | | | |
|---|---|---|---|
| 2009/0166554 A1* | 7/2009 | Radovanov | H01J 37/08 |
| | | | 250/424 |
| 2009/0200484 A1* | 8/2009 | Frosien | H01J 37/243 |
| | | | 250/396 R |
| 2009/0309041 A1* | 12/2009 | Kurunczi | H01J 37/08 |
| | | | 250/492.21 |
| 2013/0088238 A1* | 4/2013 | Julicher | G01N 27/66 |
| | | | 324/681 |
| 2017/0021198 A1 | 1/2017 | Kawrykow et al. | |
| 2017/0309465 A1* | 10/2017 | Jarrell | H01J 49/165 |
| 2019/0209870 A1* | 7/2019 | Ueno | A61N 5/1042 |
| 2019/0371563 A1* | 12/2019 | Yamamoto | H01J 37/244 |
| 2021/0210326 A1* | 7/2021 | Mizutani | H01J 49/403 |

* cited by examiner

ASYMMETRIC DUAL-MODE IONIZATION SYSTEMS AND METHODS

CROSS-REFERENCE TO RELATED APPLICATIONS

This is a continuation of U.S. patent application Ser. No. 17/219,542 filed Mar. 31, 2021, which is incorporated herein in its entirety.

BACKGROUND OF THE INVENTION

Radiation Therapy (RT) utilizes ionizing radiation to control or kill tumors, or prevent the recurrence of tumors after other medical procedures. In cancerous tumors, ionizing radiation can damage the DNA of cancerous tissue leading to cellular death. Common types of radiation therapy include radiotherapy and radiosurgery. Radiotherapy is typically delivered in relatively smaller doses, five days a week for four to six weeks. Radiosurgery is typically delivered in relatively larger doses in one to five treatments. The number and frequency of treatments is typically referred to as the fractionation schedule. Conventional radiation therapy modalities typically deliver dose rates of 0.6-180 centigray per seconds (cGy/sec). An emerging radiotherapy modality, referred to as flash, is typically delivered at a high dose rate of 40-120 Gy/sec over a period of a few seconds or less in one treatment.

Referring now to FIG. 1, an exemplary radiation therapy system is shown. The radiation therapy system 100 can include a particle source and accelerator or an energy source 110 (herein after referred to as a particle or energy source), a beam transport system 120, a beam applicator 130, an ionization chamber measurement system 140 and a patient positioning system 150. The radiation therapy system 100 typically also includes numerous other components such as vacuum components, power supply components, cooling components, mechanical support components, gantry components and the like, that are not necessary for an understanding of aspects of the present technology and therefore are not described further herein.

In one implementation, the particle or energy source 110 can include a proton, electron or other particle source and a particle accelerator to accelerate a stream of protons, electrons or other particles. In another implementation, the particle or energy source 110 can include a photon, x-ray, gamma-ray or other energy source to generator a stream of photons, x-rays, gamma-rays or other energy. The stream of particles or energy can be output from the particle or energy source 110 onto the beam transport system 120. In one implementation, the beam transport system 120 can include various bending magnets, focus magnets and the like to direct the particles along the beam transport system 120. In one implementation, the beam applicator 130 can be configured to scan the particle stream within a target area to deliver specific amount of the dose to specific areas within the target. In another implementation, the beam applicator 130 can be a multi-leaf collimator configured to scan the energy stream within the target area. In other implementation, the beam applicator 130 can be any other device for directing the particle or energy stream to the target area. The ionization chamber measurement system 140 can be configured to measure the radiation rate, flux, beam fluence or the like of the particle stream before it is directed out to the target area of the patient. The patient positioning system 150 can include a table, chair or the like that moves in one or more directions to position patients.

In one implementation, the ionization chamber measurement system 140 measures the charge from the number of ion pairs (e.g., electron and positively charged atom) created by incident radiation as the particle stream passes through the chamber. In the conventional art, the ionization chamber can include two electrodes, a high-voltage source that applies a high-voltage potential between the two electrodes, and a circuit that measures a current generated by the ion pairs as the ionizing radiation of the particle streams passes through the gas in the chamber. The conventional art ionization chamber is calibrated to indicate a radiation rate, flux, beam fluence or the like based on the measured current for a particle stream having a given range of rate, flux, fluence or the like. However, radiation therapy systems 100 are now designed to deliver particle or energy streams for different treatment modalities that have significantly different ranges of radiation rates, flux, beam fluence or the like. For example, a radiation therapy system 100 may be utilized for a first treatment modality, such as conventional radiotherapy, that delivers a dose rate of 0.6-180 cGy/sec. The radiation therapy system 100 may also be utilized for a second treatment modality, such as flash radiotherapy, that delivers a dose rate of 40-120 Gy/sec. However, enabling the two very different treatment modalities currently requires an exchange of the ionization chamber measurement system 140. After the exchange, a long calibration process is required. Therefore, switching between two different treatment modalities, such as conventional radiotherapy and flash radiotherapy, requires that the treatment room be taken out of operation for a couple of hours. Accordingly, there is a need to improve the availability of radiation therapy systems 100 when switching between different treatment modalities.

SUMMARY OF THE INVENTION

The present technology may best be understood by referring to the following description and accompanying drawings that are used to illustrate embodiments of the present technology directed toward asymmetric dual-mode ionization systems.

In one embodiment, an ionization chamber measurement system can include a high-voltage supply, a readout plate, a first high-voltage plate, a second high-voltage plate, a switch matrix and an ion charge measurement circuit. The high-voltage supply can be configured to generate a high-voltage potential. The first high-voltage plate can be disposed to form a first active volume between the first high-voltage plate and the readout plate. The second high-voltage plate can be disposed to form a second active volume between second high-voltage plate and the readout plate. The switch matrix can be configured to couple the high-voltage potential to the first high-voltage plate during a first mode, and to couple the high-voltage potential to the second high-voltage plate during a second mode. The ion charge measurement circuit can be coupled to the readout plate. A radiation stream can be configured to pass through the first and second active volumes. The ion charge measurement circuit can be configured to measure ions generated by the radiation stream passing through the first active volume during the first mode and to measure ions generated by the radiation stream passing through the second active volume during the second mode.

In another embodiment, a dual-mode ionization measurement method can include receiving an indication of a first mode or a second mode. In the first mode, a high-voltage potential can be coupled to a first high-voltage plate of an ionization chamber. The first high-voltage plate can be separated from a readout plate by a first gap. An ionizing radiation can be passed through the first gap of the ionization chamber when the first mode is indicated. Ion charge generated by the ionizing radiation passing through the first gap can be measured on the readout plate in the first mode. In the second mode, the high-voltage potential can be coupled to a second high-voltage plate of the ionization chamber. The second high-voltage plate can be separated from the readout plate by a second gap. An ionizing radiation can be passed through the second gap of the ionization chamber when the second mode is indicated. Ion charge generated by the ionizing radiation passing through the second gap can be measured on the readout plate in the second mode. A measurement of the radiation rate of the ionizing radiation can be determined as a function of the measured ion charge and the state of the ionization mode signal.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

Embodiments of the present technology are illustrated by way of example and not by way of limitation, in the figures of the accompanying drawings and in which like reference numerals refer to similar elements and in which.

DETAILED DESCRIPTION OF THE INVENTION

Figure 1:
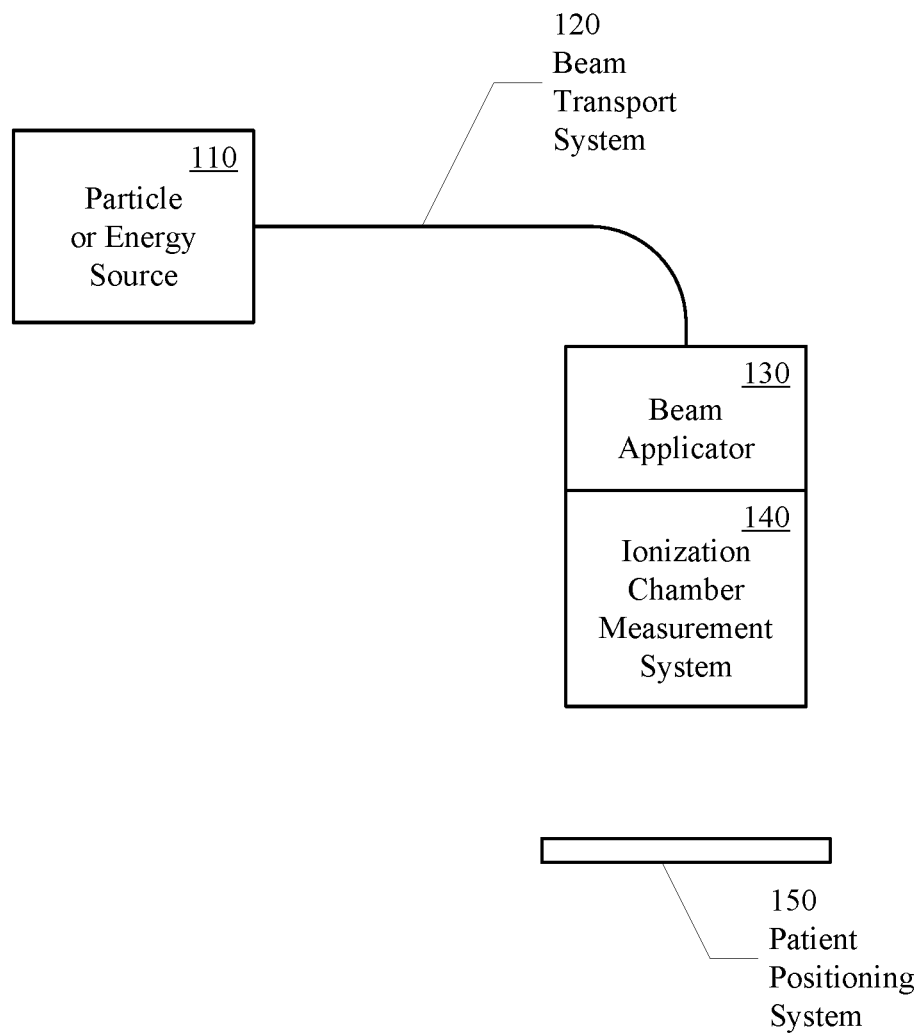
FIG. 1 shows an exemplary particle therapy system.

Reference will now be made in detail to the embodiments of the present technology, examples of which are illustrated in the accompanying drawings. While the present technology will be described in conjunction with these embodiments, it will be understood that they are not intended to limit the technology to these embodiments. On the contrary, the invention is intended to cover alternatives, modifications and equivalents, which may be included within the scope of the invention as defined by the appended claims. Furthermore, in the following detailed description of the present technology, numerous specific details are set forth in order to provide a thorough understanding of the present technology. However, it is understood that the present technology may be practiced without these specific details. In other instances, well-known methods, procedures, components, and circuits have not been described in detail as not to unnecessarily obscure aspects of the present technology.

Some embodiments of the present technology which follow are presented in terms of routines, modules, logic blocks, and other symbolic representations of operations on data within one or more electronic devices. The descriptions and representations are the means used by those skilled in the art to most effectively convey the substance of their work to others skilled in the art. A routine, module, logic block and/or the like, is herein, and generally, conceived to be a self-consistent sequence of processes or instructions leading to a desired result. The processes are those including physical manipulations of physical quantities. Usually, though not necessarily, these physical manipulations take the form of electric or magnetic signals capable of being stored, transferred, compared and otherwise manipulated in an electronic device. For reasons of convenience, and with reference to common usage, these signals are referred to as data, bits, values, elements, symbols, characters, terms, numbers, strings, and/or the like with reference to embodiments of the present technology.

It should be borne in mind, however, that these terms are to be interpreted as referencing physical manipulations and quantities and are merely convenient labels and are to be interpreted further in view of terms commonly used in the art. Unless specifically stated otherwise as apparent from the following discussion, it is understood that through discussions of the present technology, discussions utilizing the terms such as "receiving," and/or the like, refer to the actions and processes of an electronic device such as an electronic computing device that manipulates and transforms data. The data is represented as physical (e.g., electronic) quantities within the electronic device's logic circuits, registers, memories and/or the like, and is transformed into other data similarly represented as physical quantities within the electronic device.

In this application, the use of the disjunctive is intended to include the conjunctive. The use of definite or indefinite articles is not intended to indicate cardinality. In particular, a reference to "the" object or "a" object is intended to denote also one of a possible plurality of such objects. The use of the terms "comprises," "comprising," "includes," "including" and the like specify the presence of stated elements, but do not preclude the presence or addition of one or more other elements and or groups thereof. It is also to be understood that although the terms first, second, etc. may be used herein to describe various elements, such elements should not be limited by these terms. These terms are used herein to distinguish one element from another. For example, a first element could be termed a second element, and similarly a second element could be termed a first element, without departing from the scope of embodiments. It is also to be understood that when an element is referred to as being "coupled" to another element, it may be directly or indirectly connected to the other element, or an intervening element may be present. In contrast, when an element is referred to as being "directly connected" to another element, there are not intervening elements present. It is also to be understood that the term "and or" includes any and all combinations of one or more of the associated elements. It is also to be understood that the phraseology and terminology used herein is for the purpose of description and should not be regarded as limiting.

Figure 2A:
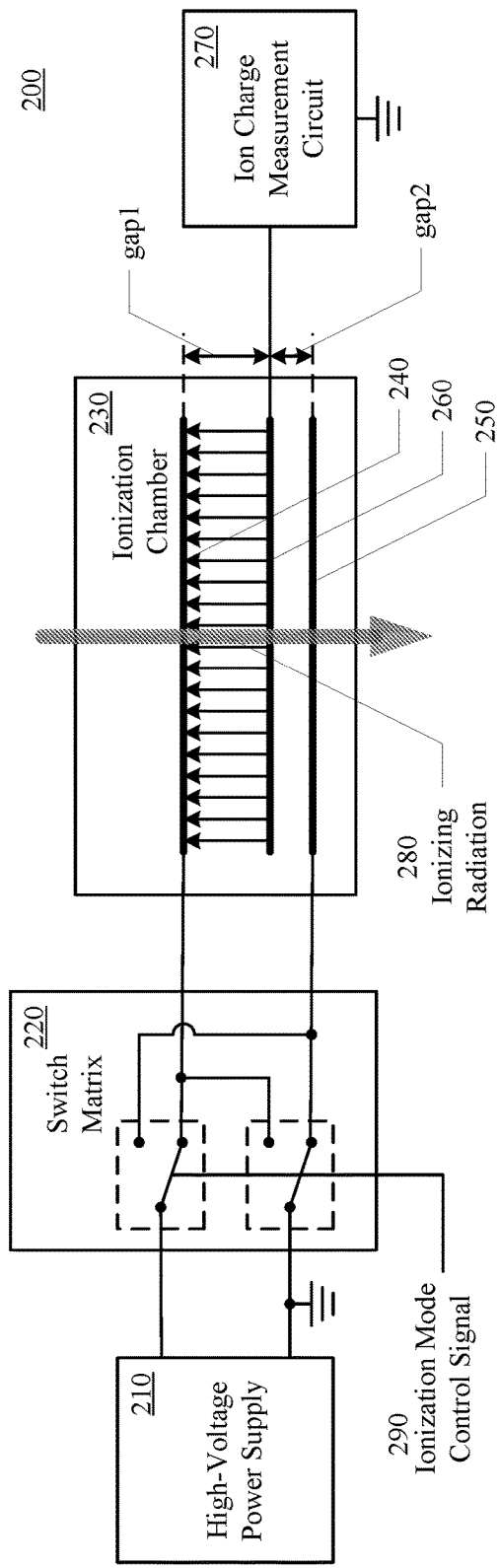
FIGS. 2A and 2B show an asymmetric dual-mode ionization system, in accordance with aspects of the present technology.
Figure 2B:
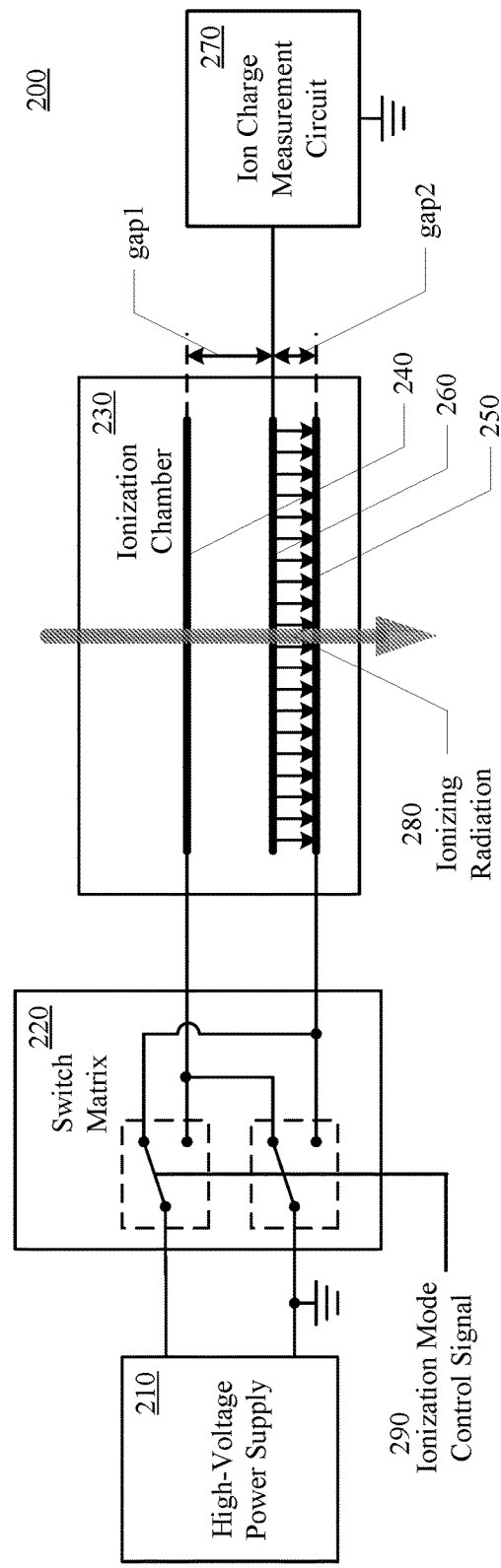

Referring now to FIGS. 2A and 2B, an asymmetric dual-mode ionization system, in accordance with aspects of the present technology, is shown. The asymmetric dual-mode ionization system can include a high-voltage supply 210, a switch matrix 220, an ionization chamber 230, a first high-voltage plate 240, a second high-voltage plate 250, a readout plate 260 and an ion charge measurement circuit 270. The asymmetric dual-mode ionization system can be configured for use in a first mode as illustrated in FIG. 2A, and a second mode as illustrated in FIG. 2B.

The ionization chamber 230 can be configured for passage of the ionizing radiation through a gas in the ionization chamber 230. The ionizing radiation can be, but is not limited to, a proton stream, an electron stream, a photon stream or other similar radiation stream. In one implementation, the ionization chamber 230 is open to the atmosphere. In other implementation, the ionization chamber 230 can be sealed and filled with one or more specific gases, and can be maintained at a predetermined pressure and temperature. In one implementation, the first high-voltage plate 240, the second high-voltage plate 250 and the readout plate 260 can be contained within the structure of the ionization chamber 230. In another implementation, the first high-voltage plate 240, the second high-voltage plate 250 and the readout plate 260 can comprise the ionization chamber 230 itself. The first high-voltage plate 240 can be disposed to form a first active volume between the first high-voltage plate 240 and the readout plate 250. The second high-voltage plate 260 can be disposed to form a second active volume between the second high-voltage plate 260 and the readout plate 250. In one implementation, the readout plate 250 can be disposed between the first high-voltage plate 240 and the second high-voltage plate 250, wherein the first high-voltage plate 240 is separated from the readout plate 250 by a first predetermined gap (gap1) and the second high-voltage plate 260 is separated from the readout plate 250 by a second predetermined gap (gap2). The first predetermined gap (gap1) can be greater than the second predetermined gap (gap2). The structure of the readout plate 260, and the first and second high-voltage plates 240, 250 within the ionization chamber 230 is also referred to herein as a double-stack dual-mode ionization chamber. In one implementation, the first high-voltage plate 240, the second high-voltage plate 250 and the readout plate 260 can be metal plates. In another implementation, the first high-voltage plate 240, the second high-voltage plate 250 and the readout plate 260 can be formed of a conductive layer disposed on an isolating substrate including, but not limited to, a polyimide layer. The first high-voltage plate 240, the second high-voltage plate 250 and the readout plate 260 can be of a given size and shape, including but not limited to round, square or rectangular. In an exemplary implementation, the first high-voltage plate 240 and the second high-voltage plate 250 can be separated from the readout plate 260 by first and second predetermined gaps (gap1, gap2) within 0.1 millimeters (mm) to 10 centimeters (cm). In other implementations the predetermined gaps may be smaller than 0.1 millimeters (mm) or larger than 10 centimeters (cm).

Ionizing radiation 280 can be configured to pass through the first and second active volumes. For example, the ionizing radiation 280 can pass through the first high-voltage plate 240, the first active volume, the readout plate 260, the second active volume, and then through the second high-voltage plate 250. For a higher radiation rate more ion pairs will be generated (e.g., gas amplification) in a given volume as compared to a lower radiation rate. Therefore, the first active volume, or first predetermined gap (gap2), can be larger for a lower radiation rate so that a number of ion pairs generated by the lower radiation rate is within a given range. Similarly, the second active volume, or second predetermined gap (gap2), can be smaller for a higher radiation rate so that the number of ion pairs generated by the higher radiation rate will be within the same given range.

The switch matrix 220 can be configured to couple the high-voltage power supply 210 to the first high-voltage plate 240 during the first mode. In a second mode, the switch matrix 220 can be configured to couple the high-voltage power supply 210 to the second high-voltage plate 250 during the second mode. For example, the switch matrix 220 can include a first switch configured to couple a high-voltage potential from the high-voltage power supply 210 to the first high-voltage plate 240 during the first mode and to the second high-voltage plate 250 during the second mode. A second switch of the switch matrix 220 can couple a ground potential to the first high-voltage plate 240 during the second mode, and to the second high-voltage plate 250 during the first mode. The switching can be automated and activated by an appropriate ionization mode control signal 290. In an exemplary implementation, the high voltage potential from the high-voltage power supply 210 applied to the first high-voltage plate 240 during the first mode and the second high-voltage plate 250 during the second mode can generate an electric field strength within the range of 100 to 1000 Volts per millimeter (V/mm) in the first and second active volumes during the respective first and second modes. As the ionizing radiation 280 passes through the first or second active volumes during the respective first and second mode, ion pairs (e.g., electrons and charged particles) are generated in the respective active volume between the respective high-voltage plate 240, 250 and the readout plate 260. The free electrons and charged particles are accelerated toward the respective high-voltage plate 240, 250 and the readout plate where they are collected by the respective plates.

In one implementation, the first mode can be characterized by a first radiation rate and the second mode can be characterized by a second radiation rate, wherein the second radiation rate is greater than the first radiation rate by an order of magnitude or greater. In one implementation, the first mode can be a conventional radiation therapy treatment modality such as, but not limited to, proton radiotherapy. The second mode can be a second radiation therapy treatment modality such as, but not limited to, flash proton radiotherapy. The first active volume, or the first predetermined gap, may be determined based upon the radiation rate (e.g., dose rate) of the ionization radiation in the first mode, and the second active volume, or the second predetermined gap, may be determined based on the radiation rate (e.g., dose rate) of the ionizing radiation in the second mode.

The ion charge measurement circuit 270 can be coupled to the readout plate 260 and configured to measure ions generated by the ionizing radiation 280 passing through the first active volume during the first mode, and to measure the ions generated by the ionizing radiation 280 passing through the second active volume during the second mode. For example, the ion charge measurement circuit 270 can measure a current generated between the readout plate 260 and ground in a first mode. In a second mode, the ion charge measurement circuit 270 can measure the current generated between the readout plate 260 and ground. In the first mode, a lower ionization radiation rate (e.g., dose rates) generates a relatively low number of ion pairs from gas amplification in a given volume. Therefore, in the large active volume in the first mode, ion pairs are generated corresponding to the ionizing radiation rate, and the resulting current can be measured by the ion charge measurement circuit 270. The measured current can be calibrated to indicate the ionizing radiation rate, beam flux, beam fluence or the like in the first mode. Similarly, in the small active volume in the second mode, ion pairs are generated corresponding to the ionizing radiation, and the resulting current can be measured by the ion charge measurement circuit 270. The measured current can be calibrated to indicate the ionizing radiation rate, beam flux, beam fluence or the like in the first mode and the second mode. For example, the measure current can be correlated to indicate the dose rate for both conventional proton radiotherapy and flash proton radiotherapy modalities without making changes to the ionization chamber 230 and/or ion charge measurement circuit 270. Therefore, the calibration can advantageously be performed once or on a periodic schedule, and not each time the mode changes, because there are no changes that need to be made with regard to ionization chamber 230 and/or ion charge measurement circuit 270.

Figure 3:
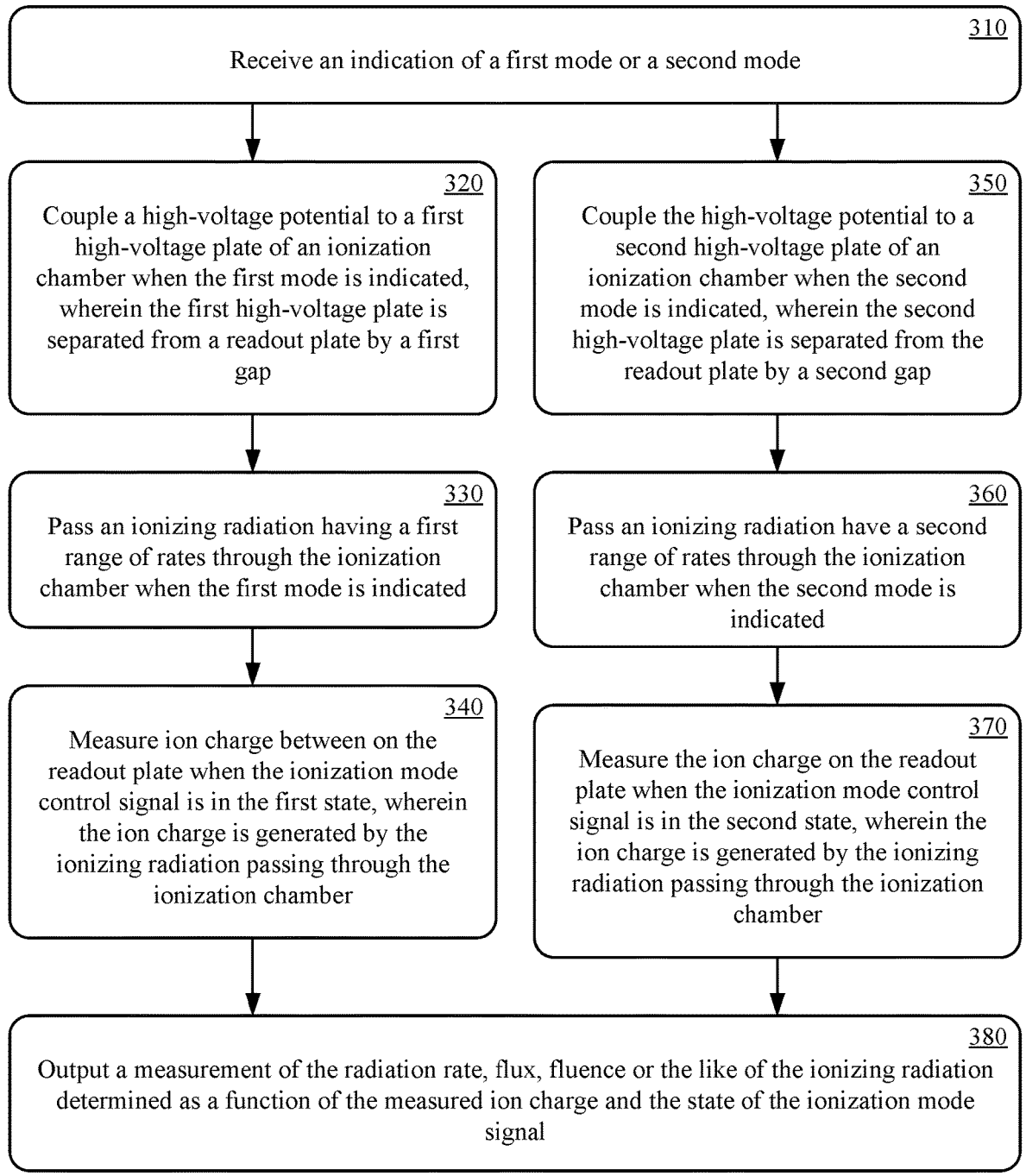
FIG. 3 shows a dual-mode ionization measurement method, in accordance with aspects of the present technology.

Referring now to FIG. 3, a dual-mode ionization measurement method, in accordance with aspects of the present technology, is shown. The dual-mode ionization measurement method can begin with receiving an indication of a first mode or a second mode, at 310. In one implementation, an ionization mode control signal, indicating a first radiation therapy mode or a second radiation therapy mode, can be received. For example, the ionization mode control signal can indicate a conventional proton radiotherapy modality or a flash proton radiotherapy modality. In another example, the ionization mode control signal can indicate a conventional electron radiotherapy modality or a flash electron radiotherapy modality. In yet another example, the ionization mode control signal can indicate a conventional photon radiotherapy modality or a flash photon radiotherapy modality.

At 320, a high-voltage potential can be coupled to a first high-voltage plate when the first mode is indicated. In one implementation, the high-voltage potential can be coupled to the first high-voltage plate of an ionization chamber when the ionization mode control signal indicates the first radiation therapy mode, where the first high-voltage plate is separated from a readout plate by a first gap. In an exemplary implementation, the high-voltage potential can generate an electric field strength within a range of 100 to 1000 V/mm across the first gap. At 330, an ionizing radiation having a first range of rates can be passed through the ionization chamber when the first mode is indicated. For example, a particle stream for a conventional proton radiotherapy modality can pass 0.6-180 cGy/sec of proton radiation through the ionization chamber when the ionization mode control signal indicates the conventional proton radiotherapy modality. In one implementation, free electrons and ions are generated by the ionizing radiation across the first gap. The free electrons and charged particles are collected by the respective first high-voltage plate and the readout plate. At 340, ion charge generated between the first high-voltage plate and the readout plate can be measured when the first mode is indicated. In one implementation, a current between the readout plate and ground can be measured when the ionizing radiation having a first range of rate passes through the ionization chamber in the first mode.

Alternatively, the high-voltage potential can be coupled to a second high-voltage plate when the second mode is indicated, at 350. In one implementation, the high-voltage potential can be coupled to the second high-voltage plate of the ionization chamber when the ionization mode control signal indicates the second radiation therapy mode, wherein the second high-voltage plate is separated from the readout plate by a second gap. In an exemplary implementation, the high-voltage potential can generate an electric field strength within a range of 100 to 1000 V/mm across the second gap. At 360, an ionizing radiation having a second range of rates can be passed through the ionization chamber when the second mode is indicated. For example, a particle stream for a flash proton radiotherapy modality can pass 40-120 Gy/sec of proton radiation through the ionization chamber when the ionization mode control signal indicates the flash proton radiotherapy modality. In one implementation, free electrons and charged particles are generated by the ionizing radiation across the second gap. The free electrons and charged particles are collected by the respective second high-voltage plate and the readout plate. At 370, ion charge generated between the second high-voltage plate and the readout plate can be measured when the second mode is indicated. In one implementation, a current between the readout plate and ground can be measured when the ionizing radiation having a second range of rates passes through the ionization chamber in the second mode.

At 380, a measurement of the rate, flux density, beam fluence or the like of the ionizing radiation, determined as a function of the measured ion charge and the corresponding first mode or second mode, can be output. In one implementation, the measured current for the given mode can be calibrated to indicate the ionizing radiation rate, flux density, beam fluence or the like. Accordingly, the measure current for example can be correlated to indicate the dose rate for both conventional proton radiotherapy and flash proton radiotherapy modalities without making changes each time the mode changes.

Referring again to FIG. 1, the dual-mode ionization chamber measurement system 200 and method 300 can be utilized in the ionization chamber measurement system 150 of radiation therapy systems 100. For example, the dual-mode ionization chamber measurement system 200 can be utilized to measure the dose rate or the like of a proton, electron or photon radiation stream of a radiation therapy system 100 that can switch between a conventional radiotherapy modality and a flash radiotherapy modality, without the need for recalibration after each switch between modalities.

The particle or energy therapy system is just one possible application of the dual-mode ionization chamber measurement system in accordance with aspects of the present technology. Other possible applications can include nuclear magnetic resonance (NMR), magnetic resonance imaging (MRI), accelerator magnets for high energy physics (HEP) research, and nuclear fusion system. The dual-mode ionization chamber measurement system in accordance with aspects of the present technology can be further utilized in any other devices and methods where particles or energy streams that have significantly different ranges of radiation rates flux, beam fluence or the like need to be measured.

The foregoing descriptions of specific embodiments of the present technology have been presented for purposes of illustration and description. They are not intended to be exhaustive or to limit the present technology to the precise forms disclosed, and obviously many modifications and variations are possible in light of the above teaching. The embodiments were chosen and described in order to best explain the principles of the present technology and its practical application, to thereby enable others skilled in the art to best utilize the present technology and various embodiments with various modifications as are suited to the particular use contemplated. It is intended that the scope of the invention be defined by the claims appended hereto and their equivalents.

What is claimed is:

1. An asymmetric dual-mode ionization chamber measurement system comprising:
   a high-voltage supply configured to generate a high-voltage potential;
   an ionization chamber including
      a readout plate,
      a first high-voltage plate disposed to form a first active volume between the first high-voltage plate and the readout plate, and
      a second high-voltage plate disposed to form a second active volume between the second high-voltage plate and the readout plate;

a switch matrix configured to selectively couple the high-voltage potential to the first high-voltage plate in a first mode, and couple the high-voltage potential to the second high-voltage plate in a second mode; and an ion charge measurement circuit coupled to the readout plate, the ion charge measurement circuit configured to measure ions generated by a radiation stream passing through the first active volume in the first mode and to measure ions generated by the radiation stream passing through the second active volume in the second mode.

2. The asymmetric dual-mode ionization chamber measurement system of claim 1, wherein:
 a range of rates of the radiation stream in the second mode is greater than a range of rates of the radiation stream in the first mode; and
 the first active volume is greater than the second active volume.

3. The asymmetric dual-mode ionization chamber measurement system of claim 1, wherein:
 the radiation stream comprises a proton radiation stream;
 the first mode comprises a conventional proton radiotherapy modality; and
 the second mode comprises a flash proton radiotherapy modality.

4. The asymmetric dual-mode ionization chamber measurement system of claim 1, wherein:
 the radiation stream comprises an electron radiation stream;
 the first mode comprises a conventional electron radiotherapy modality; and
 the second mode comprises a flash electron radiotherapy modality.

5. The asymmetric dual-mode ionization chamber measurement system of claim 1, wherein:
 the radiation stream comprises a photon radiation stream;
 the first mode comprises a conventional photon radiotherapy modality; and
 the second mode comprises a flash photon radiotherapy modality.

6. The asymmetric dual-mode ionization chamber measurement system of claim 1, wherein the switch matrix comprises:
 a first switch configured to couple the high-voltage potential to the first high-voltage plate in the first mode and couple the high-voltage potential to the second high-voltage plate in the second mode; and
 a second switch configured to couple a ground potential to the second high-voltage plate in the first mode and couple the ground potential to the first high-voltage plate in the second mode.

7. The asymmetric dual-mode ionization chamber measurement system of claim 1, wherein the ion charge measurement circuit comprises a current measurement circuit configured to measure a current generated by ions flowing between the readout plate and a ground potential in the first mode and by the ions flowing between the readout plate and the ground potential in the second mode.

8. The asymmetric dual-mode ionization chamber measurement system of claim 1, wherein the high-voltage potential generates an electric field strength between 100 and 1000 V/mm across the first active volume in the first mode and across the second active volume in the second mode.

9. An asymmetric dual-mode ionization measurement method comprising:

coupling a high-voltage potential to a first high-voltage plate of an ionization chamber in a first mode, wherein the first high-voltage plate is separated from a readout plate by a first gap;

coupling the high-voltage potential to a second high-voltage plate of the ionization chamber in a second mode, wherein the second high-voltage plate is separated from the readout plate by a second gap;

passing an ionizing radiation having a first density range through the ionization chamber in the first mode;

passing an ionizing radiation have a second density range through the ionization chamber in the second mode;

measuring ion charge generated by the ionizing radiation on the readout plate in the first mode;

measuring the ion charge generated by the ionizing radiation on the readout plate in the second mode; and outputting a measurement of a radiation rate of the ionizing radiation determined as a function of the measured ion charge and a state of an ionization mode signal.

10. The asymmetric dual-mode ionization measurement method according to claim 9, wherein:
 the ionizing radiation comprises proton radiation;
 the first mode comprises a conventional proton radiotherapy modality; and
 the second mode comprises a flash proton radiotherapy modality.

11. The asymmetric dual-mode ionization measurement method according to claim 9, wherein:
 the ionizing radiation comprises electron radiation;
 the first mode comprises a conventional electron radiotherapy modality; and
 the second mode comprises a flash electron radiotherapy modality.

12. The asymmetric dual-mode ionization measurement method according to claim 9, wherein:
 the ionizing radiation comprises photon radiation;
 the first mode comprises a conventional photon radiotherapy modality; and
 the second mode comprises a flash photon radiotherapy modality.

13. The asymmetric dual-mode ionization measurement method according to claim 9, further comprising:
 coupling a ground potential to the second high-voltage plate of the ionization chamber in the first mode; and
 coupling the ground potential to a first high-voltage plate of the ionization chamber in the second mode.

14. A radiation therapy system comprising:
 a particle or energy source;
 a beam transport system coupled to the particle or energy source;
 a beam applicator coupled to the beam transport system; and
 an ionization chamber measurement system coupled to the beam applicator, wherein the ionization chamber measurement system includes
  a high-voltage supply configured to generate a high-voltage potential,
  a readout plate,
  a first high-voltage plate disposed to form a first active volume between the first high-voltage plate and the readout plate,
  a second high-voltage plate disposed to form a second active volume between the second high-voltage plate and the readout plate,
  a switch matrix configured to selectively couple the high-voltage potential to the first high-voltage plate in a first mode, and couple the high-voltage potential to the second high-voltage plate in a second mode, and an ion charge measurement circuit coupled to the readout plate, the ion charge measurement circuit configured to measure ions generated by ionizing radiation passing through the first active volume in the first mode and to measure ions generated by the ionizing radiation passing through the second active volume in the second mode.

15. The radiation therapy system of claim 14, wherein:
the particle or energy source comprises a proton source and accelerator;
the first mode comprises a conventional proton radiotherapy modality; and
the second mode comprises a flash proton radiotherapy modality.

16. The radiation therapy system of claim 14, wherein:
the particle or energy source comprises an electron source and accelerator;
the first mode comprises a conventional electron radiotherapy modality; and
the second mode comprises a flash electron radiotherapy modality.

17. The radiation therapy system of claim 14, wherein:
the particle or energy source comprises a photon source; the first mode comprises a conventional photon radiotherapy modality; and
the second mode comprises a flash photon radiotherapy modality.

18. The radiation therapy system of claim 14, wherein the switch matrix comprises:
a first switch configured to couple the high-voltage potential to the first high-voltage plate in the first mode and couple the high-voltage potential to the second high-voltage plate in the second mode; and
a second switch configured to couple a ground potential to the second high-voltage plate in the first mode and couple the ground potential to the first high-voltage plate in the second mode.

19. The radiation therapy system of claim 14, wherein the ion charge measurement circuit comprises a current measurement circuit.

20. The radiation therapy system of claim 14, wherein the readout plate, the first high-voltage plate and the second high-voltage plate comprise conductive plates.

21. The radiation therapy system of claim 14, wherein the readout plate, the first high-voltage plate and the second high-voltage plate comprise plates of a conductive layer on an isolating substrate.

* * * * *